(12) United States Patent
Neuba et al.

(10) Patent No.: US 8,882,854 B2
(45) Date of Patent: Nov. 11, 2014

(54) REDUCTION OF AMMONIA ODOR WHEN COLORING AND/OR LIGHTENING HAIR

(71) Applicant: Henkel AG & Co. KGaA, Duesseldorf (DE)

(72) Inventors: Constanze Neuba, Grevenbroich (DE); Frank Janssen, Cologne (DE); Kota Uchida, Chiba (JP); Shoji Machida, Tokyo (JP)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 14/105,746

(22) Filed: Dec. 13, 2013

(65) Prior Publication Data
US 2014/0165300 A1    Jun. 19, 2014

(30) Foreign Application Priority Data

Dec. 14, 2012  (DE) .................. 10 2012 223 205

(51) Int. Cl.
*A61Q 5/10*       (2006.01)
*A61K 8/34*       (2006.01)
(52) U.S. Cl.
CPC .... *A61K 8/34* (2013.01); *A61Q 5/10* (2013.01)
USPC ............... 8/405; 8/406; 8/552; 8/554; 8/611; 8/619

(58) Field of Classification Search
USPC .............. 8/405, 406, 552, 554, 611, 619
See application file for complete search history.

(56) References Cited

U.S. PATENT DOCUMENTS

2012/0048288 A1*  3/2012  Reichert et al. ............... 132/208

FOREIGN PATENT DOCUMENTS

| JP | 2007-191459 A | 8/2007 |
|---|---|---|
| WO | 2005/110499 A1 | 11/2005 |
| WO | 2006/060565 A2 | 6/2006 |
| WO | 2006/060570 A2 | 6/2006 |

OTHER PUBLICATIONS

STIC Search Report dated Feb. 6, 2014.*

* cited by examiner

*Primary Examiner* — Eisa Elhilo
(74) *Attorney, Agent, or Firm* — David K. Benson

(57) ABSTRACT

Agents and methods are provided for coloring and/or lightening keratinic fibers. In one embodiment, an agent for coloring and/or lightening keratinic fibers includes, in a cosmetic carrier, (a) one or more oxidation dye precursors, (b) ammonia, (c) one or more ethoxylated fatty alcohols having a degree of ethoxylation from 80 to 120, and (d) one or more zwitterionic polymers. The agent contains no carbonates.

9 Claims, No Drawings

REDUCTION OF AMMONIA ODOR WHEN COLORING AND/OR LIGHTENING HAIR

CROSS-REFERENCE TO RELATED APPLICATIONS

This application claims priority to German Application No. 10 2012 223 205.2, filed Dec. 14, 2012, which is hereby incorporated in its entirety by reference.

TECHNICAL FIELD

The subject matter herein relates to agents for coloring and/or lightening keratinic fibers, in particular human hair, containing in a cosmetic carrier a special combination of at least one oxidation dye precursor, at least one nonionic emulsifier agent of the type of the ethoxylated fatty alcohols having a degree of ethoxylation from 80 to 120, and at least one zwitterionic polymer. Embodiments herein further relate to the use of this special combination to reduce ammonia odor before, during, and after the coloring and/or lightening operation.

BACKGROUND

One skilled in the art knows of a variety of coloring systems, depending on the required color result, for making available color-changing cosmetic agents, in particular for keratinic fibers such as e.g. human hair. For permanent, intense color results having corresponding fastness properties, so-called "oxidative" coloring agents are used. Such coloring agents usually contain oxidation dye precursors called "developer components" and "coupler components" that, under the influence of oxidizing agents such as hydrogen peroxide, form the actual dyes with one another. Oxidizing coloring agents are notable for outstanding, long-lasting color results. In addition to coloring, lightening of one's own hair color, resp. hair-bleaching, is a very special desire of many consumers. For this, the natural or artificial dyes coloring the fibers are usually decolorized oxidatively using corresponding oxidizing agents, for example hydrogen peroxide.

In order to provide satisfactory coloring and lightening performance, oxidative coloring agents resp. lightening agents generally require an alkaline pH during utilization; optimum results are achieved in particular at pH values between 8.5 and 10.5.

Until the present time, ammonia has been the alkalizing agent of choice for establishing these pH values. Not only can ammonia be used to establish the pH range necessary for dye formation, but ammonia also ensures swelling of the hair to a greater extent than all other known alkalizing agents. At the same time, ammonia acts—again to a greater extent than all other commercially usual alkalizing agents—as a penetration adjuvant.

For these reasons, when ammonia is used in oxidative coloring agents, more-intense colors and significantly better gray coverage are obtained as compared with other alkalizing agents (for example, potassium hydroxide or sodium hydroxide, alkanolamines, or carbonates such as sodium carbonate or potassium carbonate).

Because the color intensities are greater from the outset, the fastness properties of hair colors generated with the aid of ammonia are also better. In particular, colored hair achieves the best washing fastness values when ammonia has been selected as an alkalizing agent.

The applications-engineering advantages associated with the use of ammonia are so numerous that despite its unpleasant, pungent odor, ammonia is used in a large number of commercially usual oxidative coloring agents.

Extensive efforts to reduce the ammonia odor are already known from the literature. Three possibilities exist in principle for minimizing the odor: as a first possibility, the literature recites varying the alkalizing agent and thus partly or entirely replacing ammonia with odorless alternatives.

A plurality of formulations exist, for example, which employ a mixture of ammonia and monoethanolamine, or exclusively monoethanolamine, as alkalizing agents. A reduction in the ammonia content generally results, however, in poorer penetration of the dyes into the hair, which is reflected (as described above) in particular in poorer gray coverage and poorer washing fastness. If the development of particularly durable tints is paramount, the use of monoethanolamines is therefore not an option.

WO 2006060570 and WO 2006060565 propose the use of carbonates or carbonate sources as alkalizing agents in order to furnish oxidative coloring agents with little odor impact. It is likewise known in the literature, however, that carbonates in combination with oxidizing agents can damage the hair to a greater extent. The additional damage to the hair brought about by carbonates may not be much of a problem when utilizing the coloring agent on untreated resp. undamaged hair, but in the case of persons who regularly color resp. bleach their hair it can add up to serious cumulative damage. If more intense lightening and/or regular coloring is desired, the use of carbonates therefore once again does not represent a feasible alternative.

A second possibility, in principle, for reducing ammonia odor consists in the addition of special perfume substances that are intended to mask the ammonia odor. This approach is taken, for example, in WO 2005/110499. Perfume substances can be unstable under alkaline storage conditions, however, so that the risk exists that the scents may become degraded or structurally modified during storage, which is also reflected in an unpredictable change in odor. Because corresponding changes often become perceptible only after several months or even years, the employment of new resp. unknown perfumes is considered problematic.

A third general possibility for reducing ammonia odor consists in optimizing the formulation. The idea here is to select the carrier constituents of the formulation in such a way that they ensure optimum retention of ammonia in the formulation, and in that manner minimize its odor. It is once again known, however, that the formulation, the fatty substances contained in it, its emulsifier agents and surfactants, and its viscosity have a substantial influence on coloring performance. When the formulation is modified, a deterioration in coloring performance must therefore in all cases be avoided.

For example, JP 2007191459 proposes the use of cationic surfactants, phosphate esters, and aliphatic alcohols in order to reduce ammonia odor in hair coloring agents.

JP 2003040750 discloses that the ammonia odor in hair-bleaching agents is particularly low when at least 5% of a crystalline component is added to the agents.

Long-term odor minimization over the entire utilization period is, in particular, very difficult to achieve. The time span within which the user of hair colors is in contact with the coloring agent extends from production of the utilization mixture through application thereof onto the hair and the contact period, until the formulation is washed out. With usual contact times of 30 to 45 minutes, the entire process can take up to 90 minutes, at most up to two hours. An olfactory masking of ammonia which is effective over this entire time period represents the greatest challenge. It is specifically in this area that an even greater demand for optimization still exists, and an optimal capability for long-term reduction of ammonia odor is so far not known from the existing art.

The object of the present invention was therefore to make available agents for oxidative coloring and/or lightening of hair having a reduced ammonia odor. The agents are to exhibit no loss in terms of their coloring performance, in particular in terms of their gray coverage and their washing fastness. In addition, utilization of the agent is not to be associated with greater hair damage.

The object of the present invention was in particular to achieve a reduction in ammonia odor over the entire duration of use. The intention was that even after a maximum of two hours of contact, the olfactory perception of ammonia was still to be effectively minimized.

BRIEF SUMMARY

Agents and methods are provided for coloring and/or lightening keratinic fibers. In one embodiment, an agent for coloring and/or lightening keratinic fibers includes, in a cosmetic carrier, (a) one or more oxidation dye precursors, (b) ammonia, (c) one or more ethoxylated fatty alcohols having a degree of ethoxylation from 80 to 120, and (d) one or more zwitterionic polymers. The agent contains no carbonates.

In another embodiment, a method is provided for reducing an ammonia odor before, during and after a hair coloring and/or hair lightening process. The method includes applying an agent to the hair, wherein the agent includes a combination of (a) one or more oxidation dye precursors, (b) ammonia, (c) one or more ethoxylated fatty alcohols having a degree of ethoxylation from 80 to 120, and (d) one or more zwitterionic polymers, and wherein the agent contains no carbonates.

DETAILED DESCRIPTION

In the course of the work leading to this invention it has emerged, surprisingly, that it is possible to effectively minimize the olfactory perception of ammonia in agents for coloring and/or lightening keratinic fibers over the entire utilization time period if, in addition to the oxidation dyes and ammonia, a combination of special, highly ethoxylated fatty alcohol ethoxylates and special zwitterionic polymers is added to the agents.

A first subject of the present invention is therefore an agent for coloring and/or lightening keratinic fibers, in particular human hair, containing in a cosmetic carrier
(a) one or more oxidation dye precursors,
(b) ammonia,
(c) one or more ethoxylated fatty alcohols having a degree of ethoxylation from 80 to 120,
(d) one or more zwitterionic polymers,
with the provision that the agent contains no carbonates.

"Keratin-containing fibers" are understood in principle as all animal hair, e.g. wool, horsehair, angora wool, furs, feathers, and products or textiles produced therefrom. Preferably, however, the keratinic fibers are human hairs.

The term "agents for coloring and/or lightening" keratin fibers that is used according to the present invention is understood to mean oxidative coloring agents. Oxidative coloring agents contain oxidation dye precursors, so-called "developers" and "coupler components." Developers and couplers diffuse separately into the keratin fibers and, under the influence of ammonia as an alkalizing agent and an oxidizing agent (usually hydrogen peroxide), react chemically with one another to form the actual dyes. Depending on the quantity of oxidizing agent employed, the keratin fibers are simultaneously lightened to a greater or less extent during coloring, since the oxidizing agent not only initiates, the dye-forming process of the developers and couplers, but also oxidatively destroys the hair's own pigments (melanins).

Depending on the quantities of oxidation dye precursors and oxidizing agent that are used, the oxidative coloring process can therefore involve predominantly coloring (with a high dye proportion) or predominantly lightening (with a high proportion of oxidizing agent). In the latter case, the oxidation dye precursors are employed principally to tint the lightening result.

The agents according to the present invention contain the constituents essential to the invention in a cosmetic carrier, preferably in a suitable aqueous, alcoholic, or aqueous alcoholic carrier. For hair-coloring purposes such carriers are, for example, creams, emulsions, gels, or also surfactant-containing foaming solutions, for example shampoos, foam aerosols, foam formulations, or other preparations that are suitable for utilization on the hair.

As a first essential formulation constituent (a), the agents according to the present invention for coloring and/or lightening keratin fibers contain one or more oxidation dye precursors.

Categorized among the oxidation dye precursors are oxidation dye precursors of the developer type and of the coupler type. Particularly suitable oxidation dye precursors of the developer type are selected from at least one compound from the group of p-phenylenediamine, p-toluoylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)pyrazole, 2,4,5,6-tetraminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one, and physiologically acceptable salts thereof.

Particularly suitable oxidation dye precursors of the coupler type are selected from the group of 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethyl amino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino) ethanol, 2-({3-[(2-hydroxyethyl)amino]-2-methoxy-5-methylphenyl}amino)ethanol, 2-({3-[(2-hydroxyethyl) amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3- methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline, or mixtures of said compounds or physiologically acceptable salts thereof.

In a preferred embodiment, the agents according to the present invention contain one or more oxidation dye precursors (a) in a total quantity of from about 0.01 to about 4.0 wt %, preferably from about 0.1 to about 3.5 wt %, more preferably from about 0.6 to about 3.1 wt %, and very particularly preferably from about 1.2 to about 2.2 wt %, based on the total weight of the ready-to-use agent.

As an alkalizing agent essential to the invention and as a second component (b), the agents according to the present invention furthermore contain ammonia.

Ammonia is employed preferably in the form of its aqueous solution. Corresponding aqueous ammonia solutions can be about 10- to about 35-percent solutions (calculated in wt %; 100 g aqueous ammonia solution accordingly contains 10 to 35 g ammonia). Ammonia is employed preferably in the form of an about 20 to about 30 wt % solution, particularly preferably in the form of an about 25 wt % solution.

It has emerged that the olfactory perception of ammonia can be minimized particularly effectively and over a particularly long time period if there is a special quantitative ratio of ammonia (b) to the further essential formulation constituents (c) and (d). It is correspondingly particularly preferred if ammonia is used in the agent according to the present invention in a specific quantity range.

In a further particularly preferred embodiment, an agent for coloring and/or lightening keratinic fibers is therefore characterized in that it contains ammonia (b) in a quantity from about 0.25 to about 1.75 wt %, preferably from about 0.4 to about 1.4 wt %, more preferably from about 0.6 to about 1.1 wt %, and particularly preferably from about 0.7 to about 0.9 wt %, based on the total weight of the ready-to-use agent.

The aforementioned preferred and particularly preferred quantitative indications of ammonia (b) assume pure ammonia as a basis for calculation. If about 0.7 to about 0.9 wt % ammonia (b) is therefore employed very particularly preferably in the ready-to-use agent, this corresponds to the utilization of a quantity of from about 2.8 g to about 3.6 g of a 25 wt % ammonia solution in the ready-to-use coloring agent.

As already described previously, the complete or partial replacement of ammonia with alternative, odorless alkalizing agents entails a wide variety of applications-engineering disadvantages. In particular, the addition of carbonates is associated with greater hair damage. The provision therefore exists that the agents according to the present invention contain no carbonates.

"Carbonates" for purposes of the present invention are all salts that contain carbonate or hydrogen carbonate as an anion. This definition embraces inorganic carbonate salts such as sodium carbonate, sodium hydrogen carbonate, potassium carbonate, potassium hydrogen carbonate, ammonium carbonate, magnesium carbonate, or calcium carbonate. The carbonate salts of metals or transition metals also fall within the definition of the present invention. Also embraced by the definition of "carbonates" are the salts of organic cations (for example tetraalkylammonium ions) that possess as a counter ion a carbonate anion ($CO_3^{2-}$) or hydrogen carbonate anion ($HCO_3^-$).

By definition, an agent according to the present invention contains "no carbonates" if the total concentration of carbonates in the agent according to the present invention is less than about 0.1 wt %, preferably less than about 0.05 wt %, particularly preferably less than about 0.01 wt %, and extraordinarily preferably about 0 wt %, based on the total weight of the ready-to-use agent.

If ammonia is entirely or partly replaced with alkanolamines, this too is associated with applications-engineering disadvantages. The replacement of ammonia with alkanolamines can in particular lead to a deterioration in washing fastness values and in the gray coverage of specific tints.

In a further preferred embodiment, an agent for coloring and/or lightening keratinic fibers is therefore characterized in that it contains no alkanolamines.

Alkanolamines are primary, secondary, or tertiary amines having a $C_2$ to $C_6$ alkyl basic structure that carries at least one hydroxyl group. Alkanolamines that can be recited as examples are 2-aminoethan-1-ol (monoethanolamine), 2-amino-2-methylpropan-1-ol, 2-amino-2-methylpropane-1,3-diol, and triethanolamine.

By definition, an agent according to the present invention contains "no alkanolamines" if the total concentration of alkanolamines in the agent according to the present invention is less than about 0.1 wt %, preferably less than about 0.05 wt %, particularly preferably less than about 0.01 wt %, and extraordinarily preferably about 0 wt %, based on the total weight of the ready-to-use agent.

As a third formulation constituent (c) essential to the invention, the agents according to the present invention for coloring and/or lightening keratin fibers contain one or more ethoxylated fatty alcohols having a degree of ethoxylation from 80 to 120.

"Fatty alcohols" are to be understood according to the present invention as saturated or unsaturated, unbranched or branched $C_8$ to $C_{24}$ alkyl groups with hydroxy substitution. Unsaturated fatty alcohols can be mono- or polyunsaturated. In the case of an unsaturated fatty alcohol, its carbon-carbon double bond(s) can exhibit the cis- or trans-configuration.

Preferred fatty alcohols are octan-1-ol (octyl alcohol, capryl alcohol), decan-1-ol (decyl alcohol, caprinyl alcohol), dodecan-1-ol (dodecyl alcohol, lauryl alcohol), tetradecan-1-ol (tetradecyl alcohol, myristyl alcohol), hexadecan-1-ol (hexadecyl alcohol, cetyl alcohol, palmityl alcohol), octadecan-1-ol (octadecyl alcohol, stearyl alcohol), (9Z)-octadec-9-en-1-ol (oleyl alcohol), (9E)-octadec-9-en-1-ol (elaidyl alcohol), (9Z,12Z)-octadeca-9,12-dien-1-ol (linoleyl alcohol), (9Z,12Z,15Z)-octadeca-9,12,15-trien-1-ol (linolenyl alcohol), eicosan-1-ol (eicosyl alcohol, arachyl alcohol), (9Z)-eicos-9-en-1-ol (gadoleyl alcohol), (5Z,8Z,11Z,14Z)-eicosa-5,8,11,14-tetraen-1-ol (arachidonyl alcohol), docosan-1-ol (docosyl alcohol, behenyl alcohol), (13E)-docosen-1-ol (brassidyl alcohol), and (13Z)-docos-13-en-1-ol (erucyl alcohol). Within this group in turn, hexadecan-1-ol (hexadecyl alcohol, cetyl alcohol, palmityl alcohol) and octadecan-1-ol (octadecyl alcohol, stearyl alcohol) are very particularly preferred fatty alcohols.

In order to constitute the constituent (c) essential to the present invention, these fatty alcohols are ethoxylated with a degree of ethoxylation from 80 to 120.

"Ethoxylation" (also "oxyethylation") is understood as the reaction of fatty alcohols with ethylene oxide (EO). The insertion of from 80 to 120 groups of the —$CH_2$—$CH_2$—O— type per fatty alcohol molecule yields linear polyethers that carry at one end of the chain a hydroxy group and at the other end of the chain the $C_8$ to $C_{24}$ alkyl group of the fatty alcohol.

Preferred ethoxylated fatty alcohols (c) have a degree of ethoxylation from 90 to 110. It is very particularly preferred if ethoxylated fatty alcohols (c) having a degree of ethoxylation of 100 are employed.

In a further very particularly preferred embodiment, an agent for coloring and/or lightening keratinic fibers is characterized in that it contains as (an) ethoxylated fatty alcohol(s) (c) having a degree of ethoxylation from 80 to 120 one or more compounds of formula (I)

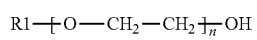
$$R1 \!-\!\!\left[\!O\!-\!CH_2\!-\!CH_2\!\right]_n\!\!-\!OH \qquad (I)$$

in which R1 denotes a saturated or unsaturated, unbranched or branched $C_8$ to $C_{24}$ alkyl group, preferably a saturated, unbranched $C_{16}$ or $C_{18}$ alkyl group, and n denotes an integer from 80 to 120, preferably an integer from 90 to 110, and particularly preferably the number 100.

In the course of the work leading to this invention it has emerged that, surprisingly, the degree of ethoxylation of the ethoxylated fatty alcohol (c) substantially influences the ability of the agent to reduce ammonia odor. For this reason, it is particularly preferred if one or more ethoxylated fatty alcohols having a very specific degree of ethoxylation are employed as (an) ethoxylated fatty alcohol(s) (c). It is very particularly preferred if one or more ethoxylated fatty alcohols from the group disclosed in the priority-establishing Application on pages 8 to 18 are used as an ethoxylated fatty alcohol (c).

A particularly advantageous and thus explicitly very particularly preferred agent for coloring and/or lightening keratinic fibers is characterized in that it contains as (an) ethoxylated fatty alcohol(s) (c) one or more compounds from the group of hexadecan-1-ol (hexadecyl alcohol, cetyl alcohol, palmityl alcohol) ethoxylated with 90 EO,
hexadecan-1-ol (hexadecyl alcohol, cetyl alcohol, palmityl alcohol) ethoxylated with 91 EO,
hexadecan-1-ol (hexadecyl alcohol, cetyl alcohol, palmityl alcohol) ethoxylated with 92 EO,
hexadecan-1-ol (hexadecyl alcohol, cetyl alcohol, palmityl alcohol) ethoxylated with 93 EO,
hexadecan-1-ol (hexadecyl alcohol, cetyl alcohol, palmityl alcohol) ethoxylated with 94 EO,
hexadecan-1-ol (hexadecyl alcohol, cetyl alcohol, palmityl alcohol) ethoxylated with 95 EO,
hexadecan-1-ol (hexadecyl alcohol, cetyl alcohol, palmityl alcohol) ethoxylated with 96 EO,
hexadecan-1-ol (hexadecyl alcohol, cetyl alcohol, palmityl alcohol) ethoxylated with 97 EO,
hexadecan-1-ol (hexadecyl alcohol, cetyl alcohol, palmityl alcohol) ethoxylated with 98 EO,
hexadecan-1-ol (hexadecyl alcohol, cetyl alcohol, pahnityl alcohol) ethoxylated with 99 EO,
hexadecan-1-ol (hexadecyl alcohol, cetyl alcohol, palmityl alcohol) ethoxylated with 100 EO,
hexadecan-1-ol (hexadecyl alcohol, cetyl alcohol, palmityl alcohol) ethoxylated with 101 EO,
hexadecan-1-ol (hexadecyl alcohol, cetyl alcohol, palmityl alcohol) ethoxylated with 102 EO,
hexadecan-1-ol (hexadecyl alcohol, cetyl alcohol, palmityl alcohol) ethoxylated with 103 EO,
hexadecan-1-ol (hexadecyl alcohol, cetyl alcohol, palmityl alcohol) ethoxylated with 104 EO,
hexadecan-1-ol (hexadecyl alcohol, cetyl alcohol, palmityl alcohol) ethoxylated with 105 EO,
hexadecan-1-ol (hexadecyl alcohol, cetyl alcohol, palmityl alcohol) ethoxylated with 106 EO,
hexadecan-1-ol (hexadecyl alcohol, cetyl alcohol, palmityl alcohol) ethoxylated with 107 EO,
hexadecan-1-ol (hexadecyl alcohol, cetyl alcohol, palmityl alcohol) ethoxylated with 108 EO,
hexadecan-1-ol (hexadecyl alcohol, cetyl alcohol, palmityl alcohol) ethoxylated with 109 EO,
hexadecan-1-ol (hexadecyl alcohol, cetyl alcohol, palmityl alcohol) ethoxylated with 110 EO,
octadecan-1-ol (octadecyl alcohol, stearyl alcohol) ethoxylated with 90 EO,
octadecan-1-ol (octadecyl alcohol, stearyl alcohol) ethoxylated with 91 EO,
octadecan-1-ol (octadecyl alcohol, stearyl alcohol) ethoxylated with 92 EO,
octadecan-1-ol (octadecyl alcohol, stearyl alcohol) ethoxylated with 93 EO,
octadecan-1-ol (octadecyl alcohol, stearyl alcohol) ethoxylated with 94 EO,
octadecan-1-ol (octadecyl alcohol, stearyl alcohol) ethoxylated with 95 EO,
octadecan-1-ol (octadecyl alcohol, stearyl alcohol) ethoxylated with 96 EO,
octadecan-1-ol (octadecyl alcohol, stearyl alcohol) ethoxylated with 97 EO,
octadecan-1-ol (octadecyl alcohol, stearyl alcohol) ethoxylated with 98 EO,
octadecan-1-ol (octadecyl alcohol, stearyl alcohol) ethoxylated with 99 EO,
octadecan-1-ol (octadecyl alcohol, stearyl alcohol) ethoxylated with 100 EO,
octadecan-1-ol (octadecyl alcohol, stearyl alcohol) ethoxylated with 101 EO,
octadecan-1-ol (octadecyl alcohol, stearyl alcohol) ethoxylated with 102 EO,
octadecan-1-ol (octadecyl alcohol, stearyl alcohol) ethoxylated with 103 EO,
octadecan-1-ol (octadecyl alcohol, stearyl alcohol) ethoxylated with 104 EO,
octadecan-1-ol (octadecyl alcohol, stearyl alcohol) ethoxylated with 105 EO,
octadecan-1-ol (octadecyl alcohol, stearyl alcohol) ethoxylated with 106 EO,
octadecan-1-ol (octadecyl alcohol, stearyl alcohol) ethoxylated with 107 EO,
octadecan-1-ol (octadecyl alcohol, stearyl alcohol) ethoxylated with 108 EO,
octadecan-1-ol (octadecyl alcohol, stearyl alcohol) ethoxylated with 109 EO,
octadecan-1-ol (octadecyl alcohol, stearyl alcohol) ethoxylated with 110 EO.

As mentioned previously, the ammonia odor of the agents according to the present invention for coloring and/or lightening hair can be reduced particularly effectively and over a long time period if there is a special quantitative ratio of ammonia (b) to the further essential formulation constituents (c) and (d).

It is correspondingly particularly advantageous if not only ammonia (b) but also the ethoxylated fatty alcohols (c) having a degree of ethoxylation from 80 to 120 are used in specific quantity ranges.

In a further preferred embodiment, an agent for coloring and/or lightening keratinic fibers is therefore characterized in that it contains one or more ethoxylated fatty alcohols (c) having a degree of ethoxylation from 80 to 120 in a total quantity from about 0.2 to about 1.5 wt %, preferably from about 0.3 to about 1.2 wt %, more preferably from about 0.4 to about 0.9 wt %, and particularly preferably from about 0.5 to about 0.8 wt %, based on the total weight of the ready-to-use agent.

As a fourth constituent essential to the invention, the agent according to the present invention contains one or more zwitterionic polymers (d).

"Polymers" are understood as macromolecules having a molecular weight of at least about 1000 g/mol, preferably at least about 2500 g/mol, particularly preferably at least about 5000 g/mol, which are made up of identical repeating organic units. Polymers are manufactured by polymerizing one type of monomer, or by polymerizing different types of monomer that differ structurally from one another. If the polymer is manufactured by polymerizing one type of monomer, the term "homopolymers" is used. If structurally different types of monomer are used in polymerization, one skilled in the art uses the term "copolymers."

The maximum molecular weight of the polymer depends on the degree of polymerization (number of polymerized monomers), and is determined inter alia by the polymerization method. For purposes of the present invention it is preferred if the maximum molecular weight of the zwitterionic polymer (d) is no more than about $10^7$ g/mol, preferably no more than about $10^6$ g/mol, and particularly preferably no more than about $10^5$ g/mol.

"Zwitterionic" polymers are understood as those polymers which contain in the macromolecule both cationic groups and anionic groups. The cationic groups contained in the macromolecule are quaternary ammonium groups. In these quaternary ammonium groups, one positively charged nitrogen atom carries four organic residues. The anionic groups are —COO⁻ groups or —SO₃⁻ groups.

In order to achieve particularly long-lasting and effective minimization of ammonia odor, it is particularly advantageous also to use the zwitterionic polymers (d) in special quantity ranges.

In a further particularly preferred embodiment, an agent for coloring and/or lightening keratinic fibers is therefore characterized in that it contains one or more zwitterionic polymers (d) in a total quantity from about 0.1 to about 1.5 wt %, preferably from about 0.2 to about 1.2 wt %, more preferably from about 0.3 to about 0.8 wt %, and particularly preferably from about 0.4 to about 0.6 wt %, based on the total weight of the ready-to-use agent.

Preferred zwitterionic polymers (d) are selected from the group of
- copolymers of dimethyldiallylammonium salts and acrylic acid, e.g. Polyquaternium-22,
- copolymers of dimethyldiallylammonium salts and methacrylic acid,
- copolymers of N,N,N-trimethyl-3-[(2-methyl-1-oxo-2-propen-1-yl)amino]-1-propanaminium salts and acrylic acid,
- copolymers of N,N,N-trimethyl-3-[(2-methyl-1-oxo-2-propen-1-yl)amino]-1-propanaminium salts and methacrylic acid,
- copolymers of N,N,N-Trimethyl-2-[(2-methyl-1-oxo-2-propen-1-yl)amino]-1-ethanaminium salts and acrylic acid,
- copolymers of N,N,N-Trimethyl-2-[(2-methyl-1-oxo-2-propen-1-yl)amino]-1-ethanaminium salts and methacrylic acid,
- copolymers of N,N,N-Trimethyl-3-[(2-methyl-1-oxo-2-propen-1-yl)amino]-1-propanaminium salts, acrylic acid, and acrylamide, e.g. Polyquaternium-53,
- copolymers of N,N,N-trimethyl-3-[(2-methyl-1-oxo-2-propen-1-yl)amino]-1-propanaminium salts, methacrylic acid, and acrylamide,
- copolymers of 1-ethenyl-3-methyl-1H-imidazolium salts, 1-ethenyl-1H-imidazole, 1-ethenyl-2-pyrrolidinone, and methacrylic acid, e.g. Polyquaternium-86,
- copolymers of 1-ethenyl-3-methyl-1H-imidazolium salts, 1-ethenyl-1H-imidazole, 1-ethenyl-2-pyrrolidinone, and acrylic acid.

Mixtures of the aforesaid preferred zwitterionic polymers (d) can also be contained in the agents according to the present invention.

Within the group of the preferred zwitterionic polymers (d), very specific zwitterionic polymers have particularly outstanding suitability for reducing ammonia odor. When these selected polymers are used, not only is the olfactory perception of the coloring agent optimized, but at the same time the washing fastness and gray coverage of the coloring agent are also improved.

For this reason, in a further explicitly very particularly preferred embodiment, an agent for coloring and/or lightening keratinic fibers is characterized in that it contains one or more zwitterionic polymers (d) that contain at least one anionic structural unit of formula (II) and at least one cationic structural unit of formula (III)

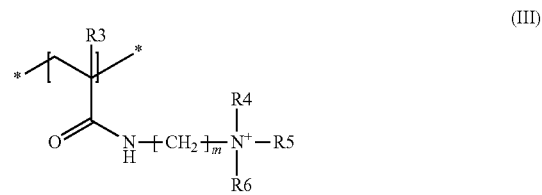

in which R2 and R3 mutually independently denote a hydrogen atom or a methyl group,
m denotes an integer from 2 to 6, preferably the numbers 2 or 3, and
the residues R4, R5, and R6 mutually independently denote a $C_1$ to $C_6$ alkyl group, preferably mutually independently denote a methyl group, an ethyl group, or a propyl group.

A particularly preferred zwitterionic polymer of this type is known by the INCI name Acrylamidopropyltrimonium Chloride/Acrylate Copolymer.

In a second embodiment that is likewise particularly preferred, an agent according to the present invention for coloring and/or lightening keratinic fibers is characterized in that it contains one or more zwitterionic polymers (d) that contain at least one anionic structural unit of formula (IV) and at least one cationic structural unit of formula (V)

-continued

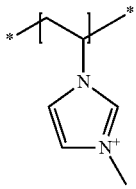
(V)

in which R7 denotes a hydrogen atom or a methyl group.

It has furthermore been found in the course of the work leading to this invention that the stated object of the present invention can be achieved completely and in satisfactory fashion if the agents according to the present invention contain further selected formulation constituents.

It has emerged, for example, that the additional presence of specific longer-chain fatty alcohols even further improves the olfactory result of the compositions according to the present invention. It is therefore preferred if the agents according to the present invention additionally contain one or more fatty alcohols from the group of arachyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), heneicosenyl alcohol (heneicosan-1-ol), behenyl alcohol (docosan-1-ol), erucyl alcohol ((13Z)-docos-13-en-1-ol), and brassidyl alcohol ((13E)-docosen-1-ol).

Particularly suitable agents contain one or more longer-chain alcohols of the aforementioned group in a total quantity of from about 1.0 to about 10.0 wt %, preferably from about 1.4 to about 8.0 wt %, more preferably from about 1.8 to about 6.0 wt %, and particularly preferably from about 2.0 to about 4.0 wt %, based on the total weight of the ready-to-use agent.

In a further preferred embodiment, an agent according to the present invention is therefore characterized in that it additionally contains one or more fatty alcohols from the group of arachyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), heneicosenyl alcohol (heneicosan-1-ol), behenyl alcohol (docosan-1-ol), erucyl alcohol ((13Z)-docos-13-en-1-ol), and brassidyl alcohol ((13E)-docosen-1-ol) in a total quantity of from about 0.1 to about 10.0 wt %, preferably from about 1.4 to about 8.0 wt %, more preferably from about 1.8 to about 6.0 wt %, and particularly preferably from about 2.0 to about 4.0 wt %, based on the total weight of the ready-to-use agent.

An agent that is characterized in that it contains in a cosmetic carrier
(a) one or more oxidation dye precursors,
(b) ammonia,
(c) one or more ethoxylated fatty alcohols having a degree of ethoxylation from 80 to 120, which are selected from the group of
  octadecan-1-ol (octadecyl alcohol, stearyl alcohol) ethoxylated with 90 EO,
  octadecan-1-ol (octadecyl alcohol, stearyl alcohol) ethoxylated with 91 EO,
  octadecan-1-ol (octadecyl alcohol, stearyl alcohol) ethoxylated with 92 EO,
  octadecan-1-ol (octadecyl alcohol, stearyl alcohol) ethoxylated with 93 EO,
  octadecan-1-ol (octadecyl alcohol, stearyl alcohol) ethoxylated with 94 EO,
  octadecan-1-ol (octadecyl alcohol, stearyl alcohol) ethoxylated with 95 EO,
  octadecan-1-ol (octadecyl alcohol, stearyl alcohol) ethoxylated with 96 EO,
  octadecan-1-ol (octadecyl alcohol, stearyl alcohol) ethoxylated with 97 EO,
  octadecan-1-ol (octadecyl alcohol, stearyl alcohol) ethoxylated with 98 EO,
  octadecan-1-ol (octadecyl alcohol, stearyl alcohol) ethoxylated with 99 EO,
  octadecan-1-ol (octadecyl alcohol, stearyl alcohol) ethoxylated with 100 EO,
  octadecan-1-ol (octadecyl alcohol, stearyl alcohol) ethoxylated with 101 EO,
  octadecan-1-ol (octadecyl alcohol, stearyl alcohol) ethoxylated with 102 EO,
  octadecan-1-ol (octadecyl alcohol, stearyl alcohol) ethoxylated with 103 EO,
  octadecan-1-ol (octadecyl alcohol, stearyl alcohol) ethoxylated with 104 EO,
  octadecan-1-ol (octadecyl alcohol, stearyl alcohol) ethoxylated with 105 EO,
  octadecan-1-ol (octadecyl alcohol, stearyl alcohol) ethoxylated with 106 EO,
  octadecan-1-ol (octadecyl alcohol, stearyl alcohol) ethoxylated with 107 EO,
  octadecan-1-ol (octadecyl alcohol, stearyl alcohol) ethoxylated with 108 EO,
  octadecan-1-ol (octadecyl alcohol, stearyl alcohol) ethoxylated with 109 EO,
  octadecan-1-ol (octadecyl alcohol, stearyl alcohol) ethoxylated with 110 EO,
(d) one or more zwitterionic polymers, and
(e) behenyl alcohol,
with the provision that the agent contains no carbonates, is correspondingly particularly preferred.

The presence of a further ethoxylated fatty alcohol (c') having a degree of ethoxylation of 30 is likewise advantageous in terms of maximum reduction of ammonia odor.

In a further embodiment that is likewise preferred, an agent according to the present invention for coloring and/or lightening keratinic fibers is therefore characterized in that it additionally contains one or more ethoxylated fatty alcohols (c') having a degree of ethoxylation of 30.

Suitable fatty alcohols having a degree of ethoxylation of 30 are
  dodecan-1-ol (dodecyl alcohol, lauryl alcohol) ethoxylated with 30 EO,
  tetradecan-1-ol (tetradecyl alcohol, myristyl alcohol) ethoxylated with 30 EO,
  hexadecan-1-ol (hexadecyl alcohol, cetyl alcohol, palmityl alcohol) ethoxylated with 30 EO,
  hexadecan-1-ol (hexadecyl alcohol, cetyl alcohol, palmityl alcohol) ethoxylated with 30 EO,
  octadecan-1-ol (octadecyl alcohol, stearyl alcohol) ethoxylated with 30 EO,
  (9Z)-octadec-9-en-1-ol (oleyl alcohol) ethoxylated with 30 EO,
  (9E)-octadec-9-en-1-ol (elaidyl alcohol) ethoxylated with 30 EO,
  (9Z,12Z)-octadeca-9,12-dien-1-ol (linoleyl alcohol) ethoxylated with 30 EO,
  eicosan-1-ol (eicosyl alcohol, arachyl alcohol) ethoxylated with 30 EO,
  docosan-1-ol (docosyl alcohol, behenyl alcohol) ethoxylated with 30 EO, and mixtures thereof.

A further particularly preferred agent is accordingly characterized in that it contains in a cosmetic carrier (a) one or more oxidation dye precursors,
(b) ammonia,
(c) one or more ethoxylated fatty alcohols having a degree of ethoxylation from 80 to 120, which are selected from the group of
  octadecan-1-ol (octadecyl alcohol, stearyl alcohol) ethoxylated with 95 EO,
  octadecan-1-ol (octadecyl alcohol, stearyl alcohol) ethoxylated with 96 EO,
  octadecan-1-ol (octadecyl alcohol, stearyl alcohol) ethoxylated with 97 EO,
  octadecan-1-ol (octadecyl alcohol, stearyl alcohol) ethoxylated with 98 EO,
  octadecan-1-ol (octadecyl alcohol, stearyl alcohol) ethoxylated with 99 EO,
  octadecan-1-ol (octadecyl alcohol, stearyl alcohol) ethoxylated with 100 EO,
  octadecan-1-ol (octadecyl alcohol, stearyl alcohol) ethoxylated with 101 EO,
  octadecan-1-ol (octadecyl alcohol, stearyl alcohol) ethoxylated with 102 EO,
  octadecan-1-ol (octadecyl alcohol, stearyl alcohol) ethoxylated with 103 EO,
  octadecan-1-ol (octadecyl alcohol, stearyl alcohol) ethoxylated with 104 EO,
  octadecan-1-ol (octadecyl alcohol, stearyl alcohol) ethoxylated with 105 EO,
(c') one or more ethoxylated fatty alcohols having a degree of ethoxylation of 30, which are selected from the group of
  dodecan-1-ol (dodecyl alcohol, lauryl alcohol) ethoxylated with 30 EO,
  tetradecan-1-ol (tetradecyl alcohol, myristyl alcohol) ethoxylated with 30 EO,
  hexadecan-1-ol (hexadecyl alcohol, cetyl alcohol, palmityl alcohol) ethoxylated with 30 EO,
  hexadecan-1-ol (hexadecyl alcohol, cetyl alcohol, palmityl alcohol) ethoxylated with 30 EO,
  octadecan-1-ol (octadecyl alcohol, stearyl alcohol) ethoxylated with 30 EO,
  (9Z)-octadec-9-en-1-ol (oleyl alcohol) ethoxylated with 30 EO,
  (9E)-octadec-9-en-1-ol (elaidyl alcohol) ethoxylated with 30 EO,
  (9Z,12Z)-octadeca-9,12-dien-1-ol (linoleyl alcohol) ethoxylated with 30 EO,
  eicosan-1-ol (eicosyl alcohol, arachyl alcohol) ethoxylated with 30 EO,
  docosan-1-ol (docosyl alcohol, behenyl alcohol) ethoxylated with 30 EO,
(d) one or more zwitterionic polymers,
with the provision that the agent contains no carbonates.

In an advantageous embodiment, the ethoxylated fatty alcohols (c) having a degree of ethoxylation from 80 to 120 and the ethoxylated fatty alcohols (c') having a degree of ethoxylation of 30 are contained in specific quantity ranges and at special ratios of (c') to (c).

Lastly, in a further embodiment that is likewise preferred, an agent according to the present invention for coloring and/or lightening keratinic fibers is characterized in that it contains the ethoxylated fatty alcohols (c') having a degree of ethoxylation of 30 and the ethoxylated fatty alcohols (c) having a degree of ethoxylation from 80 to 120 at a weight ratio (c'): (c) of at least about 1:1, preferably at a weight ratio of at least about 1.5:1, and particularly preferably at a weight ratio of at least about 2:1, based in each case on the total quantity of all ethoxylated fatty alcohols (c') contained in the ready-to-use agent and the total quantity of all ethyoxylated fatty alcohols (c) contained in the ready-to-use agent.

In addition to the ingredients recited above, the agents according to the present invention can furthermore contain the ingredients usual for oxidative coloring agents. In addition to the oxidation dye precursors, the agents can therefore also contain substantive dyes; these substantive dyes can be selected from cationic, anionic, and nonionic dyes.

Formation of the dyes in oxidative coloring agents occurs only under the influence of an oxidizing agent; hydrogen peroxide is usually used for this. In a preferred embodiment, hydrogen peroxide is used as an aqueous solution. Oxidizing agent preparations preferred according to the present invention are characterized in that they contain about 1.0 to about 23.0 wt %, more preferably about 2.5 to about 21.0 wt %, particularly preferably about 4.0 to about 20.0 wt %, and very particularly preferably about 5.0 to about 18.0 wt % hydrogen peroxide (calculated as 100-percent $H_2O_2$).

It has proven to be advantageous if the oxidizing agent preparations according to the present invention additionally contain at least one stabilizer or complexing agent in order to stabilize the hydrogen peroxide. Particularly preferred stabilizers are, in particular, EDTA and EDDS, and phosphonates, in particular 1-hydroxyethane-1,1-diphosphonate (HEDP) and/or ethylenediaminetetramethylenephosphonate (EDTMP) and/or diethylenetriaminepentamethylenephosphonate (DTPMP) resp. sodium salts thereof.

In addition to the zwitterionic polymers, the agents according to the present invention can also contain anionic polymers. Examples of suitable anionic polymers are obtainable commercially, for example, under the trade names Carbopol® or Rheothik® 11-80. The polymers marketed under the INCI name Acrylates Copolymers are also suitable anionic polymers. A preferred commercial product is, for example, Aculyn® 33 of the Rohm & Haas company. Further preferred anionic polymers are marketed by the Rohm & Haas company under the commercial name Aculyn® 22, and by the National Starch company under the commercial names Structure® 2001 and Structure® 3001.

Suitable additionally usable cationic polymers are, for example, Polyquaternium-24 (commercial product e.g. Quatrisoft® LM 200), Copolymer 845 (manufacturer: ISP), Gaffix® VC 713 (manufacturer: ISP), Gafquat® ASCP 1011, Gafquat® HS 110, Luviquat® 8155, and Luviquat® MS 370.

As naturally occurring thickening agents, nonionic guar gums such as, for example, both modified guar gums (e.g. Jaguar® HP8, Jaguar® HP60, Jaguar® HP120, Jaguar® DC 293, and Jaguar® HP105) and unmodified guar gums (e.g. Jaguar® C) can also be used. Further suitable thickening agents are scleroglucan gums or xanthan gums, gums, gum arabic, ghatti gum, karaya gum, tragacanth gum, carrageenan gum, agar-agar, locust bean flour, pectins, alginates, starch fractions and derivatives such as amylose, amylopectin, and dextrins, cellulose derivatives, e.g. methyl cellulose, carboxyalkyl celluloses, and hydroxyalkyl celluloses.

Further anionic, cationic, or amphoteric surfactants can likewise be contained in the agents according to the present invention. Preferred anionic surfactants are alkyl sulfates, alkyl ether sulfates, and ethercarboxylic acids having 10 to 18 carbon atoms in the alkyl group and up to 12 glycol ether groups in the molecule. Particularly preferred amphoteric surfactants are N-cocalkylaminopropionate, cocacylaminoethylaminopropionate, and $C_{12}$ to $C_{18}$ acylsarcosine.

Preferred cationic surfactants that are additionally contained are, for example, ammonium halides, in particular chlorides and bromides, such as alkyltrimethylammonium chlorides, dialkyldimethylammonium chlorides, and trialkylmethylammonium chlorides, for example cetyltrimethylammonium chloride, stearyltrimethylammonium chloride, distearyldimethylammonium chloride, lauryldimethylammonium chloride, lauryldimethylbenzylammonium chloride, and tricetylmethylammonium chloride, as well as the imidazolium compounds known by the INCI names Quaternium-27 and Quaternium-83.

The agents according to the present invention can moreover contain further active agents, adjuvants, and additives, for example nonionic polymers, silicones, cationic polymers, structuring agents, solvents and solubilizers, fiber-structure-improving active agents, defoamers such as silicones, anti-dandruff active agents, protein hydrolysates, vegetable oils such as macadamia nut oil, kukui nut oil, palm oil, amaranth seed oil, peach kernel oil, avocado oil, olive oil, coconut oil, rapeseed oil, sesame oil, jojoba oil, soy oil, peanut oil, evening primrose oil, and tea tree oil, light-protection agents, substances for adjusting pH, for example usual acids, in particular edible acids, vitamins, provitamins, and vitamin precursors, plant extracts, consistency agents, waxes, further swelling and penetration substances, luster agents such as ethylene glycol mono- and distearate as well as PEG-3 distearate, propellants such as propane/butane mixtures, $N_2O$, dimethyl ether, $CO_2$, and air, and antioxidants.

One skilled in the art will arrive at a selection of these further substances in accordance with the desired properties of the agents.

With regard to further optional components, as well as the quantities of those components used, reference is made expressly to the relevant manuals known to one skilled in the art, e.g. Kh. Schrader, Grundlagen and Rezepturen der Kosmetika [Cosmetics fundamentals and formulations], 2nd ed., Htithig Buch Verlag, Heidelberg, 1989.

The additional active agents and adjuvants are employed in the agents according to the present invention preferably in quantities respectively of from about 0.0001 to about 10 wt %, in particular from about 0.0005 to about 5 wt %, based on the total weight of the utilization mixture.

Coloring and lightening processes on keratin fibers usually proceed in an alkaline environment. In order to minimize stress on the keratin fibers and also on the skin, however, it is not desirable to establish too high a pH. It is therefore preferred if the pH of the ready-to-use agent is between about 6 and about 12, in particularly between about 7 and about 10.5. The pH values for purposes of the present invention are pH values that were measured at a temperature of 22° C.

The agents according to the present invention are agents for oxidative coloring and/or lightening of hair. In ready-to-use agents, the oxidation dye precursors react with the oxidizing agent, accompanied by formation of the actual dyes. The agents according to the present invention are therefore usually formulated as multi-component agents, in most cases as two-component agents. The first component contains the oxidation dye precursors and the alkalizing agent, which is mixed shortly before utilization with a second component containing the oxidizing agent. The two components are usually mixed with one another at a ratio from about 1:3 to about 3:1. This mixture of the component containing color cream/alkalizing agent and the component containing oxidizing agent is referred to as the "utilization mixture" or the "ready-to-use agent." All quantity indications with reference to the "ready-to-use agent" refer to the ready-to-use mixture of the component containing color cream/alkalizing agent and the component containing oxidizing agent.

A further subject of the present invention is the use of the combination of
(a) one or more oxidation dye precursors,
(b) ammonia,
(c) one or more ethoxylated fatty alcohols having a degree of ethoxylation from 80 to 120, and
(d) one or more zwitterionic polymers
in agents for coloring and/or lightening hair in order to reduce ammonia odor before, during, and after the coloring and/or lightening operation,
with the provision that the agent contains no carbonates.

A further subject of the present invention is a method for coloring and/or lightening keratinic fibers which is characterized in that
if desired, a pretreatment agent M1 is applied onto the fibers, then
a coloring and/or lightening agent M2 is utilized on the fibers, a further agent M3 being added if desired to the agent M2 before utilization,
said agent M2 is rinsed off the fibers after a time from 5 to 30 minutes, and
after treatment, optionally a post-treatment agent M4 is applied onto the fibers and is rinsed off again after a contact time from 2 to 25 minutes,
the agent M2 being an agent according to the present invention.

The statements made about the agents according to the present invention apply, mutatis mutandis, with regard to further preferred embodiments of the methods and uses according to the present invention.

EXAMPLES

1. Coloring Tests and Determination of Washing Fastness Values

The following formulations were produced:

| | Formulation constituents | |
|---|---|---|
| | V1 (wt %) | E1 (wt %) |
| Cetyl alcohol | 8.10 | 5.70 |
| Lanette 22 (INCI: Behenyl Alcohol) | — | 2.40 |
| Wacker Belsil ADM 1650 (INCI: Amodimethicone) | 0.5 | 0.5 |
| Eumulgin B 1 (INCI: Ceteareth-12) | 1.2 | — |
| Eumulgin B 3 (INCI: Ceteareth-30) | — | 1.2 |
| Eumulgin B 2 (INCI: Ceteareth-20) | 0.6 | — |
| Brij S 100 PA (Stearyl alcohol ethoxylated (100 EO)) | — | 0.6 |
| Cutina GMS (INCI: Glyceryl Stearate) | 0.6 | 0.6 |
| Genamin STAC (INCI: Steartrimonium Chloride) | 1.75 | 1.75 |
| Propylene glycol | 6.0 | 6.0 |
| p-Toluylenediamine sulfate | 1.50 | 1.50 |
| Resorcinol | 0.58 | 0.58 |
| m-Aminophenol | 0.16 | 0.16 |
| 3-Amino-2-methylamino-6-methoxypyridine | 0.05 | 0.05 |
| Potassium hydroxide (50%) | 0.7 | 0.7 |
| Ethylenediaminetetraacetic acid, tetrasodium salt | 0.20 | 0.20 |
| Sodium sulfite (anhydrous) | 0.30 | 0.30 |
| Vitamin C | 0.05 | 0.05 |
| Product W 37194 (N,N,N-trimethyl-3-[(1-oxo -2-propenyl)amino]-1-propanaminium chloride, polymer with sodium 2-propenoate) (INCI: Acrylamidopropyltrimonium Chloride/Acrylate Copolymer), 20 wt % aqueous solution | 2.00 | 2.00 |
| Ammonia (25 wt % aqueous solution) | 5.80 | 5.80 |
| Perfume | 0.40 | 0.40 |
| Water | to 100 | to 100 |

V1 is a comparison formulation; E1 is a formulation according to the present invention.

The color creams were each mixed at a 1:1 ratio with the following oxidizing agent formulation (OX1):

|  | Formulation constituents OX1 (wt %) |
|---|---|
| Phosphoric acid, 85% | 0.04 |
| Hydrogen peroxide (50% aqueous solution) | 12.00 |
| Emulgade F (INCI: Cetearyl Alcohol, PEG-40 Castor Oil, Sodium Cetearyl Sulfate) | 2.10 |
| Sodium benzoate | 0.04 |
| Disodium pyrophosphate | 0.30 |
| Ethylenediaminetetraacetate, disodium salt | 0.15 |
| Water | to 100 |

The utilization mixtures produced in this manner were applied with an Aplicette onto hair strands (yak belly hair) and left there for a time period from 10 to 30 minutes. The utilization mixture was then rinsed out with a shampoo and dried. The hair strands were then measured colorimetrically (Lab value measurement).

The hair strands were then washed 6 times, 12 times, and 18 times, and measured colorimetrically again after each 6, 12, and 18 hair washes (HW). The ΔE value (color distance) was calculated from the Lab values in each case using the following formula:

$$\Delta E = \sqrt{[(L_0-L_x)^2+(a_0-a_x)^2+(b_0+b_x)^2]}$$

$L_0, a_0, b_0$ Colorimetric values after 0 hair washes
$L_x, a_x, b_x$ Colorimetric values after 6, 12, resp. 18 hair washes

TABLE 1

Washing fastness values, utilization time = 10 min

|  | L value | a value | b value | ΔE | Hair washes (HW) |
|---|---|---|---|---|---|
| V1 + OX1 | 26.78 | 3.44 | 6.21 | — | 0 |
| E1 + OX1 | 24.31 | 3.02 | 5.62 | — | 0 |
| V1 + OX1 | 27.85 | 3.39 | 7.66 | 1.80 | 6 |
| E1 + OX1 | 24.57 | 3.09 | 6.55 | 0.96 | 6 |
| V1 + OX1 | 28.63 | 3.52 | 7.93 | 2.53 | 12 |
| E1 + OX1 | 25.97 | 3.23 | 7.07 | 2.22 | 12 |
| V1 + OX1 | 28.79 | 3.64 | 8.57 | 3.11 | 18 |
| E1 + OX1 | 26.23 | 3.37 | 7.55 | 2.74 | 18 |

TABLE 2

Washing fastness values, utilization time = 20 min

|  | L value | a value | b value | ΔE | Hair washes (HW) |
|---|---|---|---|---|---|
| V1 + OX1 | 18.98 | 2.79 | 3.85 | — | 0 |
| E1 + OX1 | 18.86 | 2.47 | 3.54 | — | 0 |
| V1 + OX1 | 19.47 | 2.88 | 5.55 | 1.77 | 6 |
| E1 + OX1 | 18.90 | 2.43 | 4.67 | 1.13 | 6 |
| V1 + OX1 | 20.34 | 2.82 | 5.31 | 2.00 | 12 |
| E1 + OX1 | 19.56 | 2.71 | 5.00 | 1.64 | 12 |
| V1 + OX1 | 19.80 | 2.82 | 5.43 | 1.78 | 18 |
| E1 + OX1 | 19.16 | 2.60 | 4.58 | 1.09 | 18 |

TABLE 3

Washing fastness values, utilization time = 30 min

|  | L value | a value | b value | ΔE | Hair washes (HW) |
|---|---|---|---|---|---|
| V1 + OX1 | 16.35 | 1.84 | 1.95 | — | 0 |
| E1 + OX1 | 16.38 | 1.82 | 2.17 | — | 0 |
| V1 + OX1 | 16.75 | 1.84 | 3.01 | 1.13 | 6 |
| E1 + OX1 | 16.30 | 1.80 | 2.76 | 0.60 | 6 |
| V1 + OX1 | 22.05 | 2.91 | 6.54 | 7.40 | 12 |
| E1 + OX1 | 20.42 | 2.48 | 5.00 | 4.98 | 12 |
| V1 + OX1 | 17.11 | 2.07 | 3.20 | 1.48 | 18 |
| E1 + OX1 | 16.57 | 2.08 | 3.03 | 0.92 | 18 |

The higher the ΔE value, the greater the color distance (color difference) between the respective strands when comparing their color before and after the hair washes. The higher the ΔE value, therefore, the poorer the washing fastness of the corresponding color.

It was found that the washing fastness values of the colors obtained with the formulations according to the present invention, irrespective of utilization time (10 min, 20 min, and 30 min), were consistently better than the colors obtained with the comparison formulations.

2. Determining Ammonia Odor During Utilization

The utilization mixtures previously produced (V1+OX1, E1+OX1) were each applied onto the head of a test subject. During the utilization time period, the ammonia odor was evaluated in each case by five trained persons at various points in time (directly after application at 0 min, after 10 min, after 20 min, and after 30 min). The evaluation was performed blind, meaning that the persons who performed the evaluation did not know which formulation they were evaluating at the time. The average of the individual evaluations was calculated in each case.

The ammonia odor was evaluated on a scale from 0 (virtually no odor perceptible) to 10 (very strong ammonia odor).

TABLE 4

Ammonia odor during utilization (utilization mixture)

|  | after 0 min | after 10 min | after 20 min | after 30 min |
|---|---|---|---|---|
| V1 + OX1 | 5 | 3.5 | 3.0 | 1.5 |
| E1 + OX1 | 2.25 | 2.0 | 1.5 | 1.0 |

It is evident that the ammonia odor in the context of utilization of the formulation according to the present invention, both directly after application of the formulations and after a period of 10 minutes, 20 minutes, and 30, was perceived as appreciably reduced.

3. Formulation Examples

|  | Formulation constituents (color cream) | |
|---|---|---|
|  | 1 (wt %) | 2 (wt %) |
| Cetyl alcohol | 3.6 | 4.6 |
| Lanette 22 (INCI: Behenyl Alcohol) | 2.4 | 3.0 |
| Paraffinum Liquidum | 2.1 | 2.1 |
| Eumulgin B 3 (INCI: Ceteareth-30) | 1.2 | 1.8 |
| Brij S 100 PA (Stearyl alcohol ethoxylated (100 EO)) | 0.6 | 1.0 |
| Cutina GMS (INCI: Glyceryl Stearate) | 0.6 | 0.6 |
| Propylene glycol | 6.0 | 6.0 |
| p-Toluylenediamine sulfate | 1.50 | 1.50 |
| Resorcinol | 0.58 | 0.58 |
| m-Aminophenol | 0.16 | 0.16 |
| 3-Amino-2-methylamino-6-methoxypyridine | 0.05 | 0.05 |
| Potassium hydroxide (50%) | 0.7 | 0.7 |

-continued

| Formulation constituents (color cream) | | |
|---|---|---|
| | 1 (wt %) | 2 (wt %) |
| Ethylenediaminetetraacetic acid, tetrasodium salt | 0.20 | 0.20 |
| Sodium sulfite (anhydrous) | 0.30 | 0.30 |
| Vitamin C | 0.05 | 0.05 |
| Product W 37194 ((N,N,N-trimethyl-3-[(1-oxo-2-propenyl)amino]-1-propanaminium chloride, polymer with sodium 2-propenoate) (INCI: Acrylamidopropyltrimonium Chloride/Acrylate Copolymer) 20 wt % aqueous solution | 3.75 | 3.0 |
| Ammonia (25 wt % aqueous solution) | 5.80 | 5.80 |
| Perfume | 0.40 | 0.40 |
| Water | to 100 | to 100 |

Color creams 1 and 2 were each mixed at a 1:1 ratio with the oxidizing agent formulation (OX2) and color-tested on hair.

Oxidizing Agent Formulation

| Formulation constituents | OX2 (wt %) |
|---|---|
| Sodium benzoate | 0.04 |
| Dipicolinic acid (pyridine-2,6-dicarboxylic acid) | 0.10 |
| Disodium pyrophosphate | 0.10 |
| Potassium hydroxide (50%) | 0.19 |
| Propylene glycol | 0.50 |
| Paraffinum Liquidum | 2.00 |
| Cetearyl alcohol | 3.40 |
| Ceteareth-20 | 1.00 |
| Hydrogen peroxide (50% aqueous solution) | 12.20 |
| Water | to 100 |

Both utilization mixtures (color cream 1+OX2, color cream 2+OX2) were notable for a reduced ammonia odor throughout the utilization time period.

Oxidizing Agent Formulations (all Indications in Wt %)

| Formulation constituents | | | | | |
|---|---|---|---|---|---|
| | OX3 | OX4 | OX5 | OX6 | OX7 |
| Sodium benzoate | 0.04 | 0.04 | — | — | 0.04 |
| Dipicolinic acid | 0.1 | 0.1 | 0.1 | 0.1 | 0.1 |
| Disodium pyrophosphate | 0.1 | 0.1 | 0.1 | 0.03 | 0.1 |
| Potassium hydroxide (50% aqueous solution) | 0.19 | 0.24 | 0.23 | — | 0.19 |
| Propylene glycol | 0.5 | — | — | 4.0 | 1.0 |
| 1-Hydroxyethane-1,1-diphosphonic acid (etidronic acid, 60% aqueous sol.) | 0.25 | 0.31 | 0.25 | — | 0.25 |
| Paraffinum Liquidum | 2.0 | 20 | — | — | 0.3 |
| Cetearyl alcohol | 3.6 | — | 0.5 | — | 3.4 |
| Ceteareth-20 | 1.2 | — | 0.5 | — | 1.0 |
| Hydrogen peroxide (50% aqueous solution) | 6.2 | 18.2 | 23.2 | 12.2 | 12.2 |
| Emulgade F[1] | — | — | 4.0 | — | — |
| Beeswax | — | — | 0.3 | — | — |
| Isopropyl myristate | — | — | 10 | — | — |
| Sodium hydroxide (45% aqueous sol.) | — | — | — | 0.73 | — |
| Xanthan gum (Keltrol CG-SFT) | — | — | — | 2.0 | — |
| Trimethylstearylammonium chloride | — | — | — | — | 0.29 |
| Water | to 100 | to 100 | to 100 | to 100 | to 100 |

[1]Emulgade F: Cetearyl alcohol, PEG-40 castor oil, sodium cetearyl sulfate (BASF)

The following utilization mixtures were produced:

Color cream 1+OX3, color cream 1+OX4, color cream 1+OX5, color cream 1+OX6, color cream 1+OX7, color cream 2+OX3, color cream 2+OX4, color cream 2+OX5, and color cream 2+OX6, and color cream 2+OX7.

The utilization mixture was produced respectively by mixing the color cream with the oxidizing agent formulation at a 1:1 weight ratio. The utilization mixtures produced in the manner were color-tested on hair.

Oxidizing Agent Formulations (all Indications in Wt %)

| | Formulation constituents | | | |
|---|---|---|---|---|
| | OX8 | OX9 | OX10 | OX11 |
| Dipicolinic acid | 0.1 | 0.1 | 0.1 | 0.1 |
| Disodium pyrophosphate | 0.03 | 0.03 | 0.03 | 0.03 |
| 1-Hydroxyethane-1,1-diphosphonic acid (etidronic acid, 60% aqueous sol.) | 1.5 | 1.5 | 1.5 | 1.5 |
| Ceteareth-20 | 1.0 | — | — | — |
| Hydrogen peroxide (50% aqueous solution) | 20 | 12 | 10 | 12 |
| Sodium hydroxide (45% aqueous sol.) | 0.8 | — | 0.73 | 0.83 |
| Cetyl alcohol | 3.5 | — | — | — |
| Disponil FES 77[2] | 2.5 | — | — | — |
| Aculyn 33 A[3] | 10 | 15 | — | 15 |
| Ammonia (25% aqueous sol.) | — | 0.65 | — | — |
| Sodium laureth sulfate (27% aqueous sol.) | — | 2.0 | — | 2.0 |
| Dimethicone (10%) | — | 0.067 | — | 0.067 |
| Plantacare 818 UP[4] | — | — | 15 | — |
| Cremophor CO 60[5] | — | — | 15 | — |
| Eumulgin L[6] | — | — | 0.4 | — |
| Polyquaternium-6 | — | — | 0.125 | — |
| Polyquaternium-22 (Merquat 281) | — | — | 1.0 | — |
| Fruitapone Strawberry B[7] | — | — | 0.45 | — |
| Isopropyl myristate | — | — | — | 12.16 |
| Perfume | — | — | 0.2 | — |
| Beta carotene | — | — | — | 0.125 |

-continued

| Formulation constituents | OX8 | OX9 | OX10 | OX11 |
|---|---|---|---|---|
| Marula oil | — | — | — | 0.125 |
| Controx KS C[8] | — | — | — | 0.09 |
| Water | to 100 | to 100 | to 100 | to 100 |

[2]Disponil FES 77: INCI Sodium Coceth-30 Sulfate (32-34% aqueous solution, BASF)
[3]Aculyn 33 A: INCI Acrylates Copolymer (27-29% aqueous solution, Rohm & Haas)
[4]Plantacare 818 UP: C8-16 Alkylpolyglucoside (30-50% aqueous solution, BASF)
[5]Cremophor CO 60: INCI PEG-60 Hydrogenated Castor Oil (BASF)
[6]Eumulgin L: INCI PPG-1-PEG-9 Lauryl Glycol Ether (BASF)
[7]Fruitapone Strawberry B: INCI Propylene Glycol, Aqua (Water), Citric Acid, *Fragaria Ananassa* (Strawberry) Fruit Juice, Trideceth-9, Bisabolol (Symrise)
[8]Controx KS C: INCI Tocopherol, Hydrogenated Palm Glycerides Citrate (BASF)

The following utilization mixtures were produced:
Color cream 1+OX8, color cream 1+OX9, color cream 1+OX10, color cream 1+OX11, color cream 2+OX8, color cream 2+OX9, color cream 2+OX10, and color create 2+OX11.

The utilization mixture was produced in each case by mixing the color cream with the oxidizing agent formulation at a 1:1 weight ratio. The utilization mixtures produced in the manner were color-tested on hair.

The invention claimed is:

1. An agent for coloring and/or lightening keratinic fibers comprising, in a cosmetic carrier,
   (a) one or more oxidation dye precursors,
   (b) ammonia in a quantity of from about 0.25 to about 1.75 wt %, based on the total weight of the agent,
   (c) one or more ethoxylated fatty alcohols having a degree of ethoxylation from 80 to 120, and
   (d) one or more zwitterionic polymers contain at least one anionic structural unit of formula (II) and at least one cationic structural unit of formula (III):

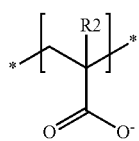
(II)

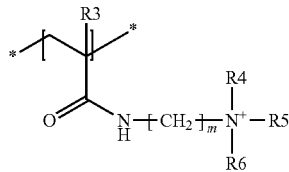
(III)

wherein R2 and R3 mutually independently denote a hydrogen atom or a methyl group, m denotes an integer from 2 to 6, and R4, R5 and R6 mutually independently denote a $C_1$ to $C_6$ alkyl group,
wherein the agent contains no carbonates.

2. The agent of claim 1 wherein the agent contains ammonia (b) in a quantity of from about 0.7 to about 0.9 wt %, based on the total weight of the agent.

3. The agent of claim 1 wherein the one or more ethoxylated fatty alcohols having a degree of ethoxylation from 80 to 120 comprises one or more compounds of formula (I)

(I)

wherein R1 is a saturated, unbranched $C_8$ to $C_{24}$ alkyl group, and wherein n is an integer from 80 to 120.

4. The agent of claim 1 wherein the agent contains one or more ethoxylated fatty alcohols having a degree of ethoxylation from 80 to 120 in a total quantity from about 0.2 to 1.5 wt %, based on the total weight of the agent.

5. The agent of claim 1 wherein the agent contains one or more zwitterionic polymers in a total quantity of from about 0.1 to 1.5 wt %, based on the total weight of the agent.

6. The agent of claim 1 further comprising one or more fatty alcohols from the group of arachyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol), and brassidyl alcohol ((13E)-docosen-1-ol) in a total quantity from about 0.1 to about 10.0 wt %, based on the total weight of the agent.

7. The agent of claim 1 further comprising one or more ethoxylated fatty alcohols (c') having a degree of ethoxylation of 30.

8. The agent of claim 1 wherein the agent includes the ethoxylated fatty alcohols (c') having a degree of ethoxylation of 30 and the ethoxylated fatty alcohols having a degree of ethoxylation from 80 to 120 at a weight ratio (c'):(c) of at least 1:1, based on the total weight of all ethoxylated fatty alcohols (c') contained in the agent and the total weight of all ethoxylated fatty alcohols (c) contained in the agent.

9. A method for reducing an ammonia odor before, during and after a hair coloring and/or hair lightening process, the method comprising:
applying an agent to the hair, wherein the agent includes a combination of (a) one or more oxidation dye precursors, (b) ammonia in a quantity of from about 0.25 to about 1.75 wt %, based on the total weight of the agent, (c) one or more ethoxylated fatty alcohols having a degree of ethoxylation from 80 to 120, and (d) one or more zwitterionic polymers contain at least one anionic structural unit of formula (II) and at least one cationic structural unit of formula (III):

(II)

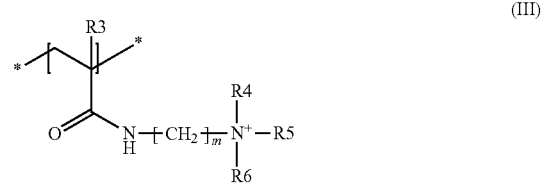
(III)

wherein R2 and R3 mutually independently denote a hydrogen atom or a methyl group, m denotes an integer from 2 to 6, and R4, R5 and R6 mutually independently denote a $C_1$ to $C_6$ alkyl group, and wherein the agent contains no carbonates.

* * * * *